(12) United States Patent
Kakizuka et al.

(10) Patent No.: US 12,011,438 B2
(45) Date of Patent: Jun. 18, 2024

(54) COMPOSITION FOR PROTECTING CARDIOMYOCYTE

(71) Applicant: Kyoto University, Kyoto (JP)

(72) Inventors: Akira Kakizuka, Kyoto (JP); Koh Ono, Kyoto (JP); Takahiro Horie, Kyoto (JP); Yuya Ide, Kyoto (JP); Naritatsu Saitou, Kyoto (JP); Takeshi Kimura, Kyoto (JP)

(73) Assignee: KYOTO UNIVERSITY, Kyoto (JP)

( * ) Notice: Subject to any disclaimer, the term of this patent is extended or adjusted under 35 U.S.C. 154(b) by 808 days.

(21) Appl. No.: 17/047,475

(22) PCT Filed: Apr. 15, 2019

(86) PCT No.: PCT/JP2019/016083
§ 371 (c)(1),
(2) Date: Oct. 14, 2020

(87) PCT Pub. No.: WO2019/203176
PCT Pub. Date: Oct. 24, 2019

(65) Prior Publication Data
US 2021/0145808 A1 May 20, 2021

(30) Foreign Application Priority Data
Apr. 16, 2018 (JP) .................. 2018-078272

(51) Int. Cl.
*A61K 31/4418* (2006.01)
*A61K 9/00* (2006.01)
*A61P 9/10* (2006.01)

(52) U.S. Cl.
CPC ........ *A61K 31/4418* (2013.01); *A61K 9/0019* (2013.01); *A61P 9/10* (2018.01)

(58) Field of Classification Search
CPC ...... A61K 31/4418; A61K 9/0019; A61P 9/10
USPC ........................................ 534/770
See application file for complete search history.

(56) References Cited

U.S. PATENT DOCUMENTS 9,573,887 B2 * 2/2017 Kakizuka .................. A61P 9/00
2013/0184241 A1 7/2013 Kakizuka et al.
2014/0148416 A1 5/2014 Kakizuka et al.
2016/0000810 A1 1/2016 Kakizuka et al.
2016/0303144 A1 10/2016 Kakizuka et al.

FOREIGN PATENT DOCUMENTS

| WO | 2012/014994 A1 | 2/2012 |
| WO | 2012/043891 A1 | 4/2012 |
| WO | 2014/129495 A1 | 8/2014 |
| WO | 2015/033981 A1 | 3/2015 |
| WO | 2015/129809 A1 | 9/2015 |

OTHER PUBLICATIONS

Lizano et al., "The valosin-containing protein is a novel mediator of mitochondrial respiration and cell survival in the heart in vivo," Scientific Reports, (7) 46324: 1-11 (2017).
Al-Obeidi et al., "Genotype-phenotype study in patients with valosin-containing protein mutations associated with multisystem proteinopathy," Clinical Genetics, 93: 119-125 (2018).
Hata et al., "KUS121, a VCP modulator, attenuates ischemic retinal cell death via suppressing endoplasmic reticulum stress," Scientific Reports, 7 (44873): 1-10 (2017).
Duan et al., "Protective effect of butin against ischemia/reperfusion-induced myocardial injury in diabetic mice: involvement of the AMPK/GSK-3β/Nrf2 signaling pathway," Scientific Reports, 7 (41491): 1-14 (2017).
Bae et al., "Hydrogen Peroxide-Responsive Nanoparticle Reduces Myocardial Ischemia/Reperfusion Injury," Journal of the American Heart Association, 5: e003697 (2016).
International Search Report issued in corresponding International Patent Application No. PCT/JP2019/016083 dated Jun. 18, 2019.
International Preliminary Report on Patentability issued in corresponding International Patent Application No. PCT/JP2019/016083 dated Oct. 29, 2020.

* cited by examiner

*Primary Examiner* — Kristin A Vajda
(74) *Attorney, Agent, or Firm* — Morgan, Lewis & Bockius LLP

(57) ABSTRACT

The inventors have found that the compounds of formula (I) protect cardiomyocytes. Accordingly, the disclosure provides a pharmaceutical composition for protecting a cardiomyocyte comprising a compound of formula (I) or an ester, oxide, pharmaceutically acceptable salt or solvate thereof. The pharmaceutical composition may be used for treating or preventing a disease associated with cardiomyocyte death, such as myocardial infarction, chronic heart failure, hypertensive heart failure, or dilated cardiomyopathy, especially for treating myocardial infarction.

9 Claims, 12 Drawing Sheets

*: P<0.05 vs. Tm 0.1µg/ml KUS 0µM

\* : P<0.05 vs. Glucose(-) KUS 0µM

*: P<0.05 vs. Control

*: P<0.05

COMPOSITION FOR PROTECTING CARDIOMYOCYTE

TECHNICAL FIELD

This application claims the benefit of priority of Japanese Patent Application No. 2018-078272, the entire contents of which are incorporated herein by reference.

The disclosure relates to a composition for protecting a cardiomyocyte.

BACKGROUND

Cardiomyocytes, which are responsible for pumping function of the heart, are damaged and eventually degenerate or necrotize in cardiac diseases such as myocardial infarction and dilated cardiomyopathy. One possible treatment for such diseases might be protecting damaged cardiomyocytes to prevent their degeneration and necrosis, since generally cardiomyocytes cannot regenerate. However, such therapy has not been established yet.

Myocardial infarction is a disease in which an occlusion or stenosis of a coronary artery reduces the blood flow to induce myocardial ischemia and necrosis. This is a major cause of chronic heart failure. Mortality and prognosis due to myocardial infarction has been improved by reperfusion therapy for treating acute myocardial infarction, in which the blood flow of the coronary artery is restored by thrombolysis or a surgical technique using a device such as a balloon catheter or stent. However, the reperfusion therapy caused a new problem of reperfusion injury, which means damage to cardiomyocytes caused by intracellular influx of calcium ions and production of reactive oxygen species during reperfusion. Along with the development of the reperfusion therapy, demand for suppressing reperfusion injury has been growing. Although some agents that decrease reactive oxygen species are known (Non-Patent Literatures 1 and 2), none have been applied to clinical practice. Suppression of reperfusion injury through any other mechanism has not been established likewise.

Certain 4-amino-naphthalene-1-sulfonic acid derivatives have a VCP (valosin-containing protein) ATPase inhibitory activity and are considered to be effective for treating various diseases (Patent Literature 1). Especially, they are known to be effective in treatment or prevention of some ocular diseases and leptin resistance (Patent Literatures 2 to 5).

REFERENCES

PATENT LITERATURE

[Patent Literature 1] WO2012/014994
[Patent Literature 2] WO2012/043891
[Patent Literature 3] WO2014/129495
[Patent Literature 4] WO2015/129809
[Patent Literature 5] WO2015/033981

NON-PATENT LITERATURE

[Non-Patent Literature 1] Duan J, et al. Protective effect of butin against ischemia/reperfusion-induced myocardial injury in diabetic mice: involvement of the AMPK/GSK-3β/Nrf2 signaling pathway. Sci Rep. 2017; 7:41491.

[Non-Patent Literature 2] Bae S, Park M, Kang C, Dilmen S, Kang T H, Kang D G, Ke Q, Lee S U, Lee D, Kang P M. Hydrogen Peroxide-Responsive Nanoparticle Reduces Myocardial Ischemia/Reperfusion Injury. J Am Heart Assoc. 2016 Nov. 14; 5(11).

SUMMARY

An object of the disclosure is to provide a composition for protecting a cardiomyocyte.

The inventors have found that VCP inhibitors can protect cardiomyocytes and are effective for treating cardiac diseases such as myocardial infarction.

Accordingly, an aspect of the disclosure provides a composition for protecting a cardiomyocyte comprising a compound of formula (I):

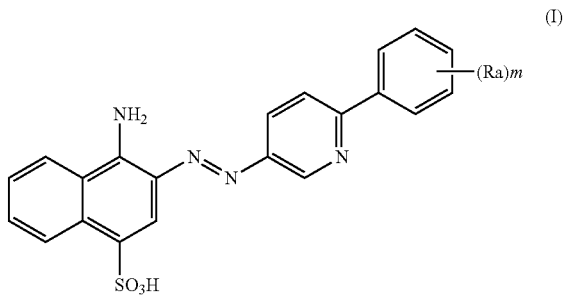

wherein
Ra is selected from the group consisting of halo, hydroxy, alkyl, halo-substituted alkyl, aryl, halo- or alkyl-substituted aryl, alkoxy, hydroxy- or carboxy-substituted alkoxy, aryloxy, halo- or alkyl-substituted aryloxy, CHO, C(O)-alkyl, C(O)-aryl, C(O)-alkyl-carboxyl, C(O)-alkylene-carboxy ester, and cyano, and
m is an integer selected from 0 to 4,
or an ester, oxide, prodrug, pharmaceutically acceptable salt or solvate thereof.

Another aspect of the disclosure provides a pharmaceutical composition for treating a myocardial infarction comprising a compound of formula (I), or an ester, oxide, prodrug, pharmaceutically acceptable salt or solvate thereof.

According to the disclosure, a composition for protecting a cardiomyocyte is provided.

DETAILED DESCRIPTION

Figure 1:
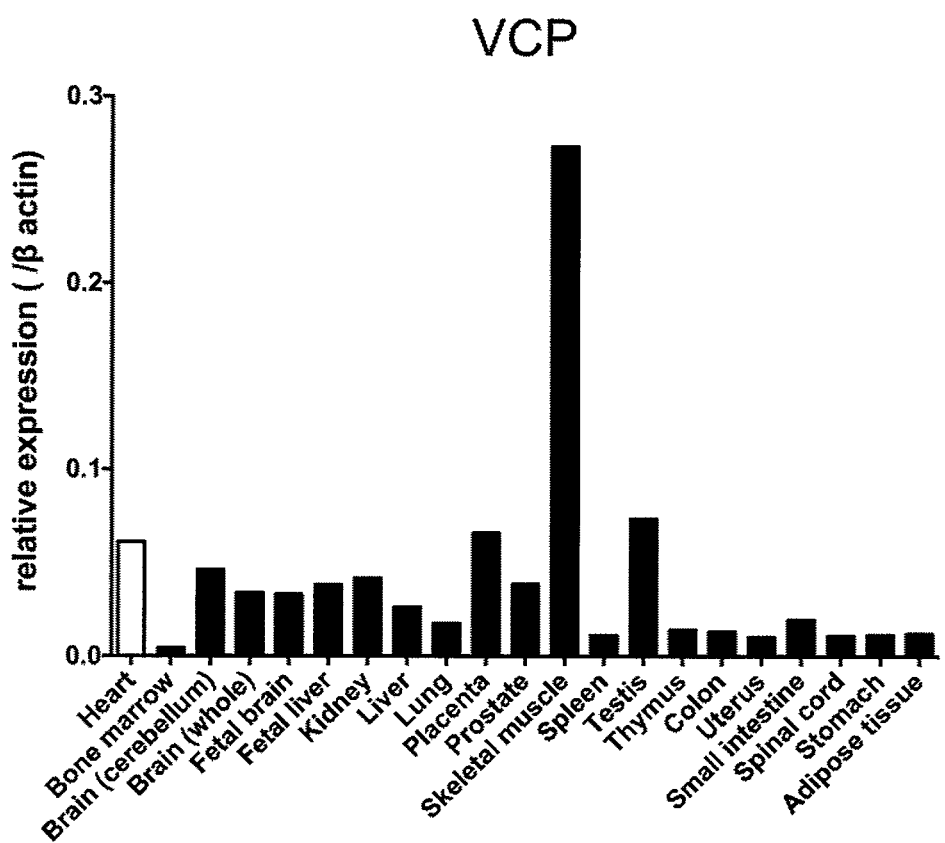
FIG. 1 shows the expression levels of VCP in human organs.

When a numerical value is accompanied with the term "about", the value is intended to represent any value in the range of −10% of the value to +10% of the value. For example, "about 20" means "a value from 18 to 22." A range defined with values of the lower and upper limits covers all values from the lower limit to the upper limit, including the values of the both limits. When a range is accompanied with the term "about", the both limits are read as accompanied with the term. For example, "about 20 to 30" is read as "18 to 33."

Unless otherwise defined, the terms used herein are read as generally understood by those skilled in the technical fields such as organic chemistry, medical sciences, pharmaceutical sciences, molecular biology, and microbiology. Several terms used herein are defined as below. The definitions herein take precedence over the general understanding.

The term "alkyl" refers to a monovalent saturated aliphatic hydrocarbyl group having 1 to 10, preferably 1 to 6, carbon atoms. Examples of the alkyl groups include, but are not limited to, linear and branched hydrocarbyl groups, such as methyl, ethyl, n-propyl, isopropyl, n-butyl, isobutyl, sec-butyl, t-butyl, n-pentyl, and neopentyl.

The term "substituted" as a word qualifying a name of a group indicates that one or more hydrogen atoms of the group are, identically or differently, replaced with one or more designated substituents.

The term "alkylene" refers to a divalent saturated aliphatic hydrocarbyl group having 1 to 10, preferably 1 to 6, carbon atoms. Alkylene groups include branched and straight chain hydrocarbyl groups.

The term "alkoxy" refers to an —O-alkyl group in which the alkyl group is as defined herein. Examples of the alkoxy groups include, but are not limited to, methoxy, ethoxy, n-propoxy, isopropoxy, n-butoxy, t-butoxy, sec-butoxy, and n-pentoxy.

The term "aryl" refers to a monovalent aromatic carbocyclic group of 6 to 14 carbon atoms having a single ring (e.g., phenyl) or multiple condensed rings (e.g., naphthyl or anthryl). Typical aryl groups include phenyl and naphthyl.

The term "aryloxy" refers to an —O-aryl group in which the aryl group is as defined herein. Examples of the aryloxy groups include phenoxy and naphthoxy.

The term "cyano" refers to the —CN group.

The term "carboxyl" or "carboxy" refers to the —COOH group or a salt thereof.

The term "carboxy ester" refers to a —C(O)O-alkyl group in which the alkyl group is as defined herein.

The term "halo" refers to a halogen, especially fluoro, chloro, bromo, or iodo.

The term "hydroxy" refers to the —OH group.

A substituent that is not explicitly defined herein is named by describing the name of the terminal functional group of the substituent first and sequentially describing the adjacent functional group(s) toward the point binding to the rest of the compound, unless otherwise indicated. For example, the substituent "arylalkyloxycarbonyl" refers to (aryl)-(alkyl)-O—O(O)—.

Some compounds of formula (I) have enantiomers or diastereomers, depending on arrangements of their substituents. Some compounds of formula (I) may be provided as racemic mixtures or may be provided in stereoisomerically pure forms separated by a known method. Some compounds of formula (I) may be tautomers.

The term "ester" refers to an ester that hydrolyzes in vivo, which may break down readily in a human body to leave the parent compound or a salt thereof. Suitable esters include, for example, those derived from pharmaceutically acceptable aliphatic carboxylic acids, especially alkanoic, alkenoic, cycloalkanoic, and alkanedioic acids, in which each alkyl or alkenyl group has, for example, not more than six carbon atoms. Examples of the esters include formates, acetates, propionates, butyrates, acrylates, and ethylsuccinates.

The term "oxide" refers to an oxide in which a nitrogen in a heteroaryl group is oxidized to form N-oxide.

The term "prodrug" refers to a prodrug of a compound which is, within the scope of sound medical judgment, suitable for use in contact with human and animal tissues without an undue adverse effect such as toxicity, irritation, and allergic response, commensurate with a reasonable benefit/risk ratio, and effective in its intended use. A prodrug is rapidly transformed in vivo, for example by hydrolysis in blood, to yield a parent compound represented by the formula above. A general discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

The term "pharmaceutically acceptable salt" may indicate a salt of a compound of formula (I) with an inorganic or organic acid. Preferred salts include salts with inorganic acids, such as hydrochloric acid, hydrobromic acid, phosphoric acid, and sulfuric acid, and salts with organic carboxylic acids and sulfonic acids, such as acetic acid, trifluoroacetic acid, propionic acid, maleic acid, fumaric acid, malic acid, citric acid, tartaric acid, lactic acid, benzoic acid, methanesulfonic acid, ethanesulfonic acid, benzenesulfonic acid, toluenesulfonic acid, naphthalene sulfonic acid, and naphthalene disulfonic acid.

Pharmaceutically acceptable salts also include salts with conventional bases, such as alkali metal salts, e.g., sodium and potassium salts, alkaline earth metal salts, e.g., calcium and magnesium salts, ammonium salts derived from ammonia and organic amines, e.g., diethylamine, triethylamine, ethyldiisopropylamine, procaine, dibenzylamine, N-methylmorpholine, dihydroabiethylamine, methylpiperidine, L-arginine, creatine, choline, L-lysine, ethylenediamine, benzathine, ethanolamine, meglumine, and tromethamine, especially a sodium salt.

The term "solvate" means a compound of formula (I) which is coordinated with a solvent molecule in a solid or liquid state to form a complex. A suitable solvate is a hydrate.

The term "compound of formula (I)" as used herein is intended to include its esters, oxides, prodrugs, pharmaceutically acceptable salts, and solvates, as long as the context allows it.

In an embodiment, each Ra radical in formula (I) is independently selected from the group consisting of halo, hydroxy, alkyl, halo-substituted alkyl, and alkoxy.

In an embodiment, each Ra radical in formula (I) is independently selected from the group consisting of halo and alkyl.

In an embodiment, formula (I) has two Ra radicals which are halo and alkyl.

In an embodiment, the compound of formula (I) is selected from the compounds listed in Table 1 below:

TABLE 1

| No. | Compound Name |
|---|---|
| 1 | 4-amino-3-(6-phenylpyridine-3-ylazo)naphthalene-1-sulfonic acid |
| 2 | 4-amino-3-(6-p-tolylpyridine-3-ylazo)naphthalene-1-sulfonic acid |
| 3 | 4-amino-3-(6-m-tolylpyridine-3-ylazo)naphthalene-1-sulfonic acid |
| 4 | 4-amino-3-(6-o-tolylpyridine-3-ylazo)naphthalene-1-sulfonic acid |
| 5 | 4-amino-3-(6-biphenyl-2-ylpyridine-3-ylazo)naphthalene-1-sulfonic acid |
| 6 | 3-[6-(2-acetylphenyl)pyridine-3-ylazo]-4-aminonaphthalene-1-sulfonic acid |
| 7 | 3-[6-(3-acetylphenyl)pyridine-3-ylazo]-4-aminonaphthalene-1-sulfonic acid |
| 8 | 3-[6-(4-acetylphenyl)pyridine-3-ylazo]-4-aminonaphthalenesulfonic acid |
| 9 | 4-amino-3-[6-(2,4-dichlorophenyl)pyridine-3-ylazo]naphthalene-1-sulfonic acid |
| 10 | 4-amino-3-[6-(2-trifluoromethylphenyl)pyridine-3-ylazo]naphthalene-1-sulfonic acid |
| 11 | 4-amino-3-[6-(4-trifluoromethylphenyl)pyridine-3-ylazo]naphthalene-1-sulfonic acid |
| 12 | 4-amino-3-[6-(2-chlorophenyl)pyridine-3-ylazo]naphthalene-1-sulfonic acid |
| 13 | 4-amino-3-[6-(3-chlorophenyl)pyridine-3-ylazo]naphthalene-1-sulfonic acid |
| 14 | 4-amino-3-[6-(4-chlorophenyl)pyridine-3-ylazo]naphthalene-1-sulfonic acid |
| 15 | 4-amino-3-[6-(2-methoxyphenyl)pyridine-3-ylazo]naphthalene-1-sulfonic acid |
| 16 | 4-amino-3-[6-(4-methoxyphenyl)pyridine-3-ylazo]naphthalene-1-sulfonic acid |
| 17 | 4-amino-3-[6-(2-isopropoxyphenyl)pyridine-3-ylazo]naphthalene-1-sulfonic acid |
| 18 | 4-amino-3-[6-(4-isopropoxyphenyl)pyridine-3-ylazo]naphthalene-1-sulfonic acid |
| 19 | 4-amino-3-[6-(2-phenoxyphenyl)pyridine-3-ylazo]naphthalene-1-sulfonic acid |
| 20 | 4-amino-3-[6-(3-methoxyphenyl)pyridine-3-ylazo]naphthalene-1-sulfonic acid |
| 21 | 4-amino-3-[6-(2,3-dimethylphenyl)pyridine-3-ylazo]naphthalene-1-sulfonic acid |
| 22 | 4-amino-3-[6-(2,5-dimethylphenyl)pyridine-3-ylazo]naphthalene-1-sulfonic acid |
| 23 | 4-amino-3-[6-(3,5-dimethylphenyl)pyridine-3-ylazo]naphthalene-1-sulfonic acid |
| 24 | 4-amino-3-[6-(3-trifluoromethylphenyl)pyridine-3-ylazo]naphthalene-1-sulfonic acid |
| 25 | 4-{4-[5-(1-amino-4-sulfonaphthalene-2-ylazo)pyridine-2-yl]phenyl}-4-oxobutyric acid |
| 26 | 4-amino-3-(6-biphenyl-3-ylpyridine-3-ylazo)naphthalene-1-sulfonic acid |
| 27 | 4-amino-3-[6-(3-cyanophenyl)pyridine-3-ylazo]naphthalene-1-sulfonic acid |
| 28 | 4-amino-3-[6-(4-cyanophenyl)pyridine-3-ylazo]naphthalene-1-sulfonic acid |
| 29 | 4-amino-3-[6-(3,5-bistrifluoromethylphenyl)pyridine-3-ylazo]naphthalenesulfonic acid |
| 30 | 4-amino-3-[6-(4-benzoylphenyl)pyridine-3-ylazo]naphthalene-1-sulfonic acid |
| 31 | 4-amino-3-[6-(2-propoxyphenyl)pyridine-3-ylazo]naphthalene-1-sulfonic acid |
| 32 | 4-amino-3-[6-(4-fluoro-2-methylphenyl)pyridine-3-ylazo]naphthalene-1-sulfonic acid |
| 33 | 4-amino-3-[6-(5-fluoro-2-propoxyphenyl)pyridine-3-ylazo]naphthalene-1-sulfonic acid |
| 34 | 4-amino-3-[6-(2-fluoro-6-propoxyphenyl)pyridine-3-ylazo]naphthalene-1-sulfonic acid |

TABLE 1-continued

| No. | Compound Name |
|---|---|
| 35 | 4-amino-3-[6-(4-fluoro-2-propoxyphenyl)pyridine-3-ylazo]naphthalene-1-sulfonic acid |
| 36 | 4-amino-3-[6-(5-fluoro-2-methylphenyl)pyridine-3-ylazo]naphthalene-1-sulfonic acid |
| 37 | 4-amino-3-[6-(2-fluoro-5-methylphenyl)pyridine-3-ylazo]naphthalene-1-sulfonic acid |
| 38 | 4-amino-3-[6-(2-butoxyphenyl)pyridine-3-ylazo]naphthalene-1-sulfonic acid |
| 39 | 4-amino-3-[6-(2-hexyloxyphenyl)pyridine-3-ylazo]naphthalene-1-sulfonic acid |
| 40 | 4-amino-3-[6-(4-butylphenyl)pyridine-3-ylazo]naphthalene-1-sulfonic acid |
| 41 | 4-amino-3-[6-(2-hydroxyphenyl)pyridine-3-ylazo]naphthalene-1-sulfonic acid |
| 42 | 4-amino-3-{6-[2-(6-hydroxyhexyloxy)phenyl]pyridine-3-ylazo}naphthalene-1-sulfonic acid |
| 43 | 4-{2-[5-(1-amino-4-sulfonaphthalene-2-ylazo)pyridine-2-yl]phenoxy}butyric acid |
| 44 | 4-amino-3-{6-[2-(3-hydroxypropoxy)phenyl]pyridine-3-ylazo}naphthalene-1-sulfonic acid |
| 45 | 4-amino-3-[6-(2-isobutoxyphenyl)pyridine-3-ylazo]naphthalene-1-sulfonic acid |
| 46 | 4-amino-3-[6-(5-chloro-2-hydroxyphenyl)pyridine-3-ylazo]naphthalene-1-sulfonic acid |
| 47 | 4-amino-3-[6-(4-methylbiphenyl-2-yl)pyridine-3-ylazo]naphthalene-1-sulfonic acid |
| 48 | 4-amino-3-[6-(4'-chloro-4-methylbiphenyl-2-yl)pyridine-3-ylazo]naphthalene-1-sulfonic acid |
| 49 | 4-amino-3-[6-(4,3',5'-trimethylbiphenyl-2-yl)pyridine-3-ylazo]naphthalene-1-sulfonic acid |
| 50 | 4-amino-3-[6-(3'-chloro-4-methylbiphenyl-2-yl)pyridine-3-ylazo]naphthalene-1-sulfonic acid |
| 51 | 4-amino-3-[6-(2,6-dimethylphenyl)pyridine-3-ylazo]naphthalene-1-sulfonic acid |
| 52 | 4-amino-3-[6-(3-formyl-2-isopropoxy-5-methylphenyl)pyridine-3-ylazo] naphthalene-1-sulfonic acid |
| 53 | 4-amino-3-[6-(3-formyl-2-butoxy-5-methylphenyl)pyridine-3-ylazo] naphthalene-1-sulfonic acid |

In an embodiment, the active ingredient is 4-amino-3-[6-(4-fluoro-2-methylphenyl)pyridine-3-ylazo]naphthalene-1-sulfonic acid, which is represented by the following formula:

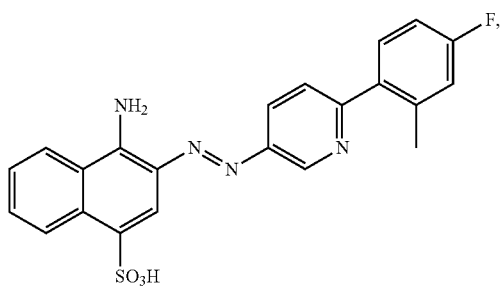

or an ester, oxide, prodrug, pharmaceutically acceptable salt or solvate thereof, especially the sodium salt.

The characteristics of the compounds of formula (I), especially the compounds listed above, and the methods for synthesizing them are described in WO2012/014994 (Patent Literature 1) in detail.

As demonstrated by the Examples below, the compounds of formula (I) can protect cardiomyocytes. Accordingly, an aspect of the disclosure provides a composition for protecting a cardiomyocyte comprising a compound of formula (I). The term "protecting a cardiomyocyte" or "cardiomyocyte protection" as used herein means suppressing cardiomyocyte death and/or suppressing ischemic injury and/or reperfusion injury of a cardiomyocyte or progression thereof. In an embodiment, by protecting a cardiomyocyte a cardiac function can be maintained and/or impairment of a cardiac function can be suppressed, and thus a cardiac disease associated with cardiomyocyte death, such as myocardial infarction, chronic heart failure, hypertensive heart failure, or dilated cardiomyopathy, can be treated or prevented.

The compounds of formula (I) can effectively inhibit impairment of cardiac functions even when they are administered via a single intracoronary administration during reperfusion, as demonstrated in the Examples in which effects of a compound of formula (I) in treatment of myocardial infarction were extensively tested. Accordingly, an aspect of the disclosure provides a pharmaceutical composition for treating myocardial infarction comprising a compound of formula (I). Furthermore, since the compounds of formula (I) can decrease the area of myocardial necrosis in a patient with myocardial infarction and thus reduce the risk of developing cardiac failure, the compounds of formula (I) may be used for treating or preventing cardiac failure caused by myocardial infarction or cardiac failure subsequent to myocardial infarction, especially chronic cardiac failure.

The term "treating" or "treatment" as used herein means that in a subject suffering from a disease a cause of the disease is reduced or removed, progression of the disease is delayed or stopped, and/or a symptom of the disease is reduced, alleviated, ameliorated, or removed.

The term "preventing" or "prevention" as used herein means that in a subject, especially a subject that is susceptible to a disease but has not been affected with the disease yet, the disease onset is prevented or the possibility of the disease onset is decreased.

Examples of the subjects that are susceptible to a cardiac disease but have not been affected with it yet include subjects having risk factors such as aging, family history of a coronary artery disease, smoking, hypertension, obesity, impaired glucose tolerance, hypercholesterolemia, hypertriglyceridemia, hypo-HDL cholesterolemia, metabolic syndrome, stress, and insufficient sleep. Examples of the subjects that are susceptible to myocardial infarction but have not been affected with it yet include subjects having risk factors such as smoking, hypercholesterolemia, diabetes, hypertension, family history of angina or myocardial infarction, aging, stress, obesity, gout, hyperuricemia, hemodialysis, hyperhomocysteinemia, and a periodontal disease. Examples of the subjects that are susceptible to chronic heart failure but have not been affected with it yet include subjects suffering from diseases such as coronary artery diseases, cardiomyopathy, valvular heart diseases, and hypertension, especially subjects suffering from myocardial infarction. Examples of the subjects that are susceptible to hypertensive heart failure but have not been affected with it yet include subjects suffering from hypertension. Examples of the subjects that are susceptible to dilated cardiomyopathy but have not been affected with it yet include subjects having genetic predispositions to dilated cardiomyopathy.

The subjects of the treatment or prevention include animals, typically mammals (e.g., humans, mice, rats, hamsters, rabbits, cats, dogs, cows, sheep, or monkeys), especially humans.

The pharmaceutical composition may be administered in any way through a generally known administration route, for example, by oral administration, parenteral administration, injection, or infusion. The composition may be in a dosage form suitable for each administration route. In an embodiment, the pharmaceutical composition is administered intracoronarily.

Dosage forms suitable for oral administration include granules, fine granules, powders, coated tablets, tablets, suppositories, fine powders, capsules, microcapsules, chewable tablets, liquids, suspensions, and emulsions. Dosage forms suitable for injection may be common dosage forms, e.g., those suitable for administration in the coronary arteryies, intravenous injection, infusion, or formulations for extended release of active ingredients. Dosage forms for administration in the coronary arteryies, intravenous injection, or infusion include aqueous and non-aqueous injectable solutions, which may comprise excipients, such as antioxidants, buffers, bacteriostatic agents, or isotonic agents; and aqueous and non-aqueous injectable suspensions, which may comprise excipients, such as suspending agents or thickening agents. Such dosage forms may be provided as liquids in sealed ampoules or vials, or provided as lyophilized products and prepared immediately prior to use by adding sterile liquids such as water for injection. The injectable solutions or suspensions may be prepared from powders, granules, or tablets.

Such dosage forms can be manufactured by formulating active ingredients by conventional methods. If necessary for the formulation, any one of various pharmaceutically acceptable excipients may be added. Any excipient may be used in accordance with the employed dosage form. Examples of the excipients include buffering agents, surfactants, stabilizers, preservatives, fillers, diluents, additives, disintegrants, binders, coating agents, lubricants, lubricating agents, flavoring agents, sweeteners, and solubilizers.

The dosage and the number of doses of the pharmaceutical composition may be appropriately set by those skilled in the art so that an effective amount of a compound of formula (I) is administered to the subject, on the basis of factors such as the animal species, health condition, age, and weight of the subject, the administration route, and the employed dosage form. Those skilled in the art may easily determine the effective amount in a given situation by routine experimentation, which is within the range of ordinary skill and determination of clinicians. For example, a compound of formula (I) may be administered in the range of about 0.001 to 1000 mg/kg body weight/day, about 0.01 to 300 mg/kg body weight/day, about 0.1 to 100 mg/kg body weight/day, about 1 to 100 mg/kg body weight/day, about 2 to 50 mg/kg body weight/day, about 2.5 to 20 mg/kg body weight/day, about 2.5 to 10 mg/kg body weight/day, or about 5 to 10 mg/kg body weight/day. In an embodiment, the pharmaceutical composition is administered once or more, especially once, during reperfusion after myocardial infarction.

In an embodiment, the pharmaceutical composition is administered intracoronarily once during reperfusion after myocardial infarction. In such a case a compound of formula (I) may be administered in the range of about 0.01 to 100 mg/kg body weight, about 0.05 to 50 mg/kg body weight, about 0.1 to 50 mg/kg body weight, about 0.1 to 20 mg/kg body weight, about 0.1 to 10 mg/kg body weight, about 1 to 10 mg/kg body weight, about 2 to 10 mg/kg body weight, about 2.5 to 10 mg/kg body weight, about 2.5 to 5 mg/kg body weight, or about 5 to 10 mg/kg body weight:

The compounds of formula (I) may be used alone or in combination with at least one further active ingredient, especially an active ingredient for treating or preventing a cardiac disease such as myocardial infarction. For example, the pharmaceutical composition may comprise at least one active ingredient in addition to a compound of formula (I).

When some ingredients are used in combination, a dosage form containing all the ingredients or a combination of dosage forms containing the ingredients separately may be employed. The ingredients may be simultaneously or sequentially administered or any ingredient may be administered at a later time point, as long as the ingredients are used for protecting a cardiomyocyte or preventing and/or treating a cardiac disease. Two or more further active ingredients may be used in combination. Examples of the active ingredients suitable for use in combination include anti-inflammatory agents, vasodilators, thrombolytic agents, antiplatelet agents, anticoagulants, and statins.

A non-drug therapy may be combined with the administration of a compound of formula (I). Examples of the suitable therapies include coronary intervention (PCI) using a devise such as balloon catheter, stent, or drug-eluting stent (DES), surgical procedures such as thrombus aspiration, gene therapy, and regenerative therapy.

An aspect of the disclosure provides a method for protecting a cardiomyocyte comprising administering a compound of formula (I) to a subject in need thereof.

An aspect of the disclosure provides a compound of formula (I) for use in protecting a cardiomyocyte.

An aspect of the disclosure provides use of a compound of formula (I) for protecting a cardiomyocyte.

An aspect of the disclosure provides use of a compound of formula (I) for manufacturing a pharmaceutical composition for protecting a cardiomyocyte.

An aspect of the disclosure provides a method for treating myocardial infarction comprising administering a compound of formula (I) to a subject in need thereof.

An aspect of the disclosure provides a compound of formula (I) for use in treating myocardial infarction.

An aspect of the disclosure provides use of a compound of formula (I) for treating myocardial infarction.

An aspect of the disclosure provides use of a compound of formula (I) for manufacturing a pharmaceutical composition for treating myocardial infarction.

For example, the disclosure provides the following embodiments.

[1] A pharmaceutical composition for protecting a cardiomyocyte, comprising a compound of formula (I):

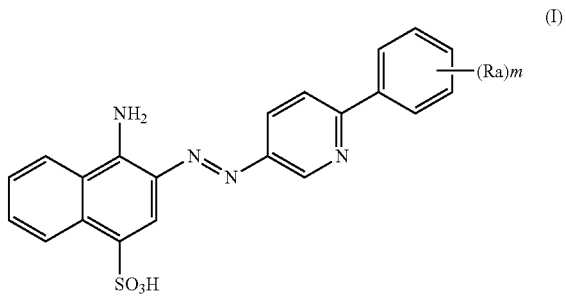

wherein
Ra is selected from the group consisting of halo, hydroxy, alkyl, halo-substituted alkyl, aryl, halo- or alkyl-substituted aryl, alkoxy, hydroxy- or carboxy-substituted alkoxy, aryloxy, halo- or alkyl-substituted aryloxy, CHO, C(O)-alkyl, C(O)-aryl, C(O)-alkyl-carboxyl, C(O)-alkylene-carboxy ester, and cyano, and
m is an integer selected from 0 to 4,
or an ester, oxide, pharmaceutically acceptable salt or solvate thereof.

[2] The pharmaceutical composition according to item 1, wherein the protecting the cardiomyocyte comprises suppressing death of the cardiomyocyte.

[3] The pharmaceutical composition according to item 1 or 2, for treating myocardial infarction, chronic heart failure, hypertensive heart failure, or dilated cardiomyopathy.

[4] The pharmaceutical composition according to any one of items 1 to 3, for treating myocardial infarction.

[5] A pharmaceutical composition for treating myocardial infarction, comprising a compound of formula (I):

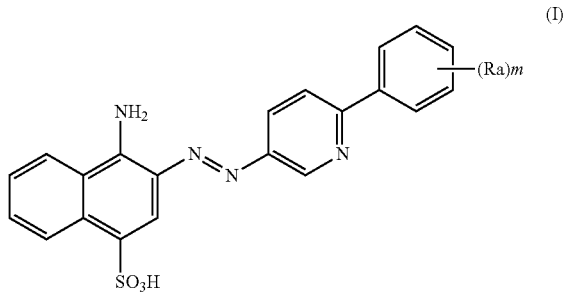

wherein
Ra is selected from the group consisting of halo, hydroxy, alkyl, halo-substituted alkyl, aryl, halo- or alkyl-substituted aryl, alkoxy, hydroxy- or carboxy-substituted alkoxy, aryloxy, halo- or alkyl-substituted aryloxy, CHO, C(O)-alkyl, C(O)-aryl, C(O)-alkyl-carboxyl, C(O)-alkylene-carboxy ester, and cyano, and
m is an integer selected from 0 to 4,
or an ester, oxide, pharmaceutically acceptable salt or solvate thereof.

[6] The pharmaceutical composition according to item 5, for further treating or preventing heart failure.

[7] The pharmaceutical composition according to item 5 or 6, for further treating or preventing chronic heart failure.

[8] The pharmaceutical composition according to any one of items 1 to 7, wherein each Ra radical is independently selected from the group consisting of halo, hydroxy, alkyl, halo-substituted alkyl, and alkoxy.

[9] The pharmaceutical composition according to any one of items 1 to 8, wherein each Ra radical is independently selected from the group consisting of halo and alkyl.

[10] The pharmaceutical composition according to any one of items 1 to 9, wherein formula (I) has two Ra radicals which are halo and alkyl.

[11] The pharmaceutical composition according to any one of items 1 to 10, wherein the compound of formula (I) is selected from the compounds listed in Table 1.

[12] The pharmaceutical composition according to any one of items 1 to 11, wherein the compound of formula (I) is 4-amino-3-[6-(4-fluoro-2-methylphenyl)pyridine-3-ylazo]naphthalene-1-sulfonic acid.

[13] The pharmaceutical composition according to any one of items 1 to 12, wherein the composition is administered intracoronarily.

[14] The pharmaceutical composition according to any one of items 1 to 13, wherein the composition is administered during reperfusion after myocardial infarction.

[15] The pharmaceutical composition according to any one of items 1 to 14, wherein the composition is administered once during reperfusion after myocardial infarction.

[16] The pharmaceutical composition according to any one of items 13 to 15, wherein about 0.01 to 100 mg/kg body weight of the compound of formula (I) is administered.

[17] The pharmaceutical composition according to any one of items 13 to 16, wherein about 1 to 10 mg/kg body weight of the compound of formula (I) is administered.

[18] The pharmaceutical composition according to any one of items 13 to 17, wherein about 2 to 10 mg/kg body weight of the compound of formula (I) is administered.

The entire contents of the documents cited herein are incorporated herein by reference.

The embodiments described above are non-limiting and may be modified without deviating from the scope of the invention as defined by the appended claims. The following examples are non-limiting and provided only for describing the invention.

EXAMPLES

In the test examples, the following compound was employed.
KUS121: 4-amino-3-[6-(4-fluoro-2-methylphenyl)pyridine-3-ylazo]naphthalene-1-sulfonic acid sodium salt
KUS121 was prepared by the method disclosed in WO2012/014994 (Patent Literature 1).

Test 1: Expression of VCP in Human Organs
Expression levels of VCP in human organs were quantified by qPCR using human Total RNA Master Panel II (Clontech Laboratories, Inc.) and total RNA: human adipose (BioChain Institute Inc.). First, 1 μg of each RNA sample was reverse transcribed into cDNAs using Verso cDNA Synthesis Kit (Thermo Fisher Scientific). The cDNAs were analyzed by qPCR with Step One Plus (Thermo Fisher Scientific) and THUNDERBIRD qPCR Mix (TOYOBO) to determine the expression levels of VCP. The results are shown in FIG. 1. The expression level of VCP in the heart was relatively high and comparable to that in the central nervous system.

Figure 2:
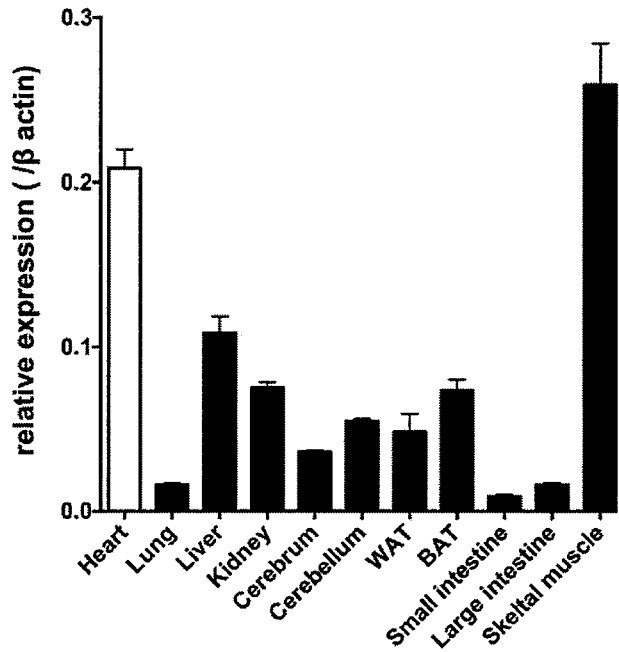
FIG. 2 shows the expression levels of VCP in mouse organs.

Test 2: Expression of VCP in Mouse Organs
Organs were isolated from 8-week-old C57BL/6J mice (Japan SLC, Inc.) and RNAs were extracted using TriPure Isolation Reagent (Roche) according to the manufacturer's protocol. Then 1 μg of each RNA sample was reverse transcribed into cDNAs using Verso cDNA Synthesis Kit. The cDNAs were analyzed by qPCR with Step One Plus and THUNDERBIRD qPCR Mix to determine the expression levels of VCP. The results are shown in FIG. 2. The expression level was relatively high in the heart.

Figure 3:
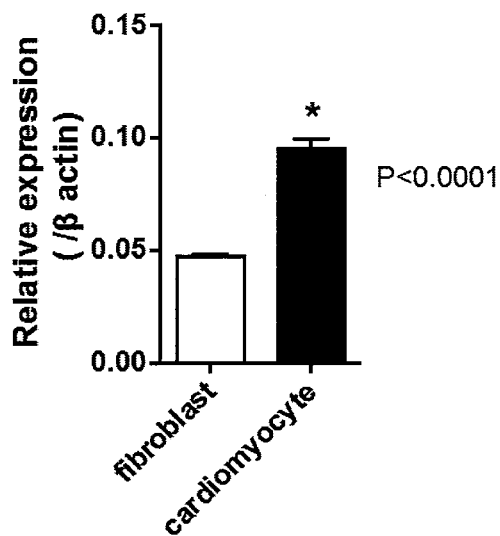
FIG. 3 shows the expression levels of VCP in cardiomyocytes and fibroblasts isolated from mouse hearts.

Test 3: Expression of VCP in Mouse Hearts
The hearts were isolated from 1-day-old neonatal C57BL/6J mice and treated with collagenase. The obtained cells were separated into cardiomyocytes and fibroblasts by FACS using Mito Tracker GreenFM (M7514, Thermo Fisher Scientific) and Thy1.2-APC (eBioscience, Inc.). The expression levels of VCP were quantified by qPCR using the same procedure as in Test 2. The results are shown in FIG. 3. The expression level was high in the cardiomyocytes.

Figure 4:
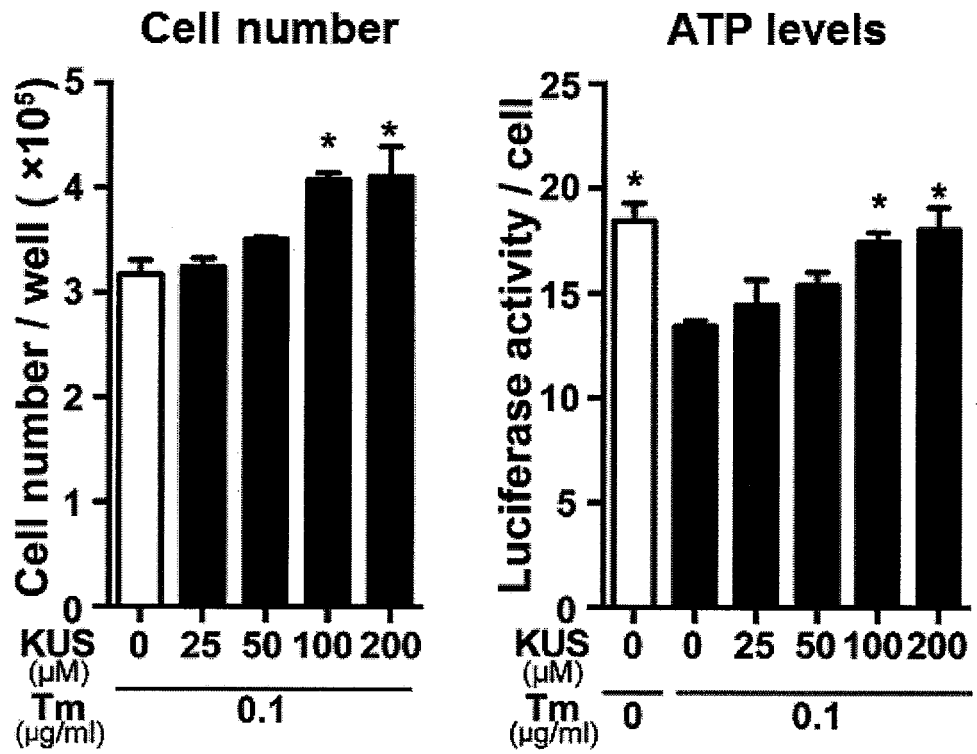
FIG. 4 shows the cell numbers and ATP levels of rat cardiomyoblasts cultured under ER stress with tunicamycin. To KUS121(+) groups 25, 50, 100, or 200 μM KUS121 was added. *: P<0.05 vs. Tm(+) KUS(−)

Test 4: Effects of KUS121 in Rat Cardiomyoblasts
H9C2 cells, rat cardiomyoblasts, were cultured in Dulbecco's modified Eagle's medium (DMEM) supplemented with 5% fetal bovine serum in the presence of 0.1 pg/mL tunicamycin (Sigma-Aldrich Co. LLC), which induces ER stress, and 25, 50, 100, or 200 pM KUS121 for 24 hours. The cells were counted by Countess II (Thermo Fisher Scientific). The intracellular ATP levels were measured using "Cell" ATP Assay reagent (TOYO B-Net Co., LTD). The luciferase activities, which indicate ATP levels, were measured with ARVO X3 (PerkinElmer, Inc.). The results are shown in FIG. 4. The cell number was increased depending on the dose of KUS121. The ATP level was decreased in the presence of tunicamycin, but increased depending on the dose of KUS121.

Figure 5:
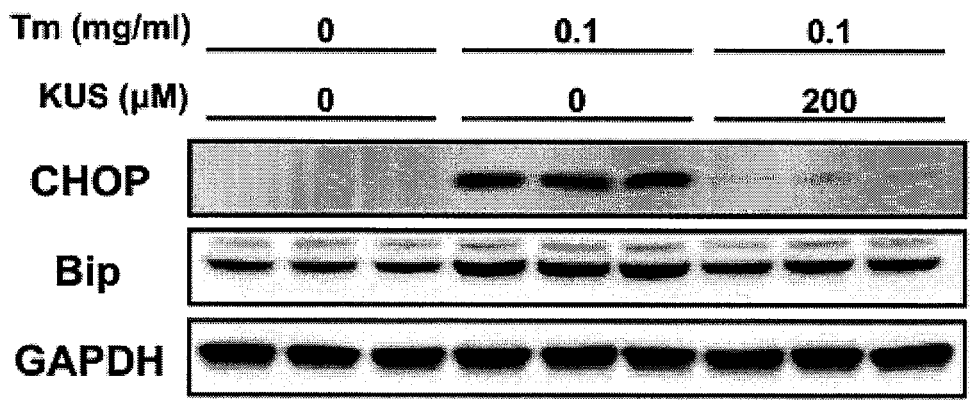
FIG. 5 shows the results of Western blotting of CHOP and Bip in rat cardiomyoblasts cultured under ER stress with tunicamycin. To KUS121(+) group 200 μM KUS121 was added.

The cells cultured as above were subjected to Western blotting. Proteins were extracted from the cells using a lysis buffer containing 100 mM Tris-HCl (pH 7.4), 75 mM NaCl, and 1% Triton X-100 (Nacalai Tesque) to which Complete Mini protease inhibitor cocktail (Roche), 0.5 mM NaF, and 10 mM $Na_3VO_4$ were added immediately before the use. After the protein concentrations were measured with BCA protein assay kit (Bio-Rad, 5000006JA), 15 μg of the protein samples were separated in NuPAGE 4-12% Bis-Tris Mini gels (Thermo Fisher Scientific) and transferred to Protran nitrocellulose transfer membrane (Whatman). The membrane was blocked with PBS containing 5% skim milk for 30 minutes, incubated with primary antibodies overnight at 4° C., washed with PBS-0.05% Tween-20 (PBS-T), incubated with secondary antibodies for 1 hour at room temperature, and washed with PBS-T. Pierce Western Blotting Substrate (Thermo Fisher Scientific) or Pierce Western Blotting Substrate plus (Thermo Fisher Scientific) were reacted with the secondary antibodies for producing colors, and the color intensities were measured by LAS-4000 Mini system (Fuji Film). The primary antibodies were CHOP (sc575, Santa Cruz Biotechnology, Inc.), Bip (#3183, Cell Signaling Technology, Inc.), GAPDH (#2118, Cell Signaling Technology, Inc.) and β-actin (Sigma-Aldrich Co. LLC). The results are shown in FIG. 5. The expressions of CHOP and Bip, ER stress markers, were suppressed in the presence of KUS121.

Figure 6:
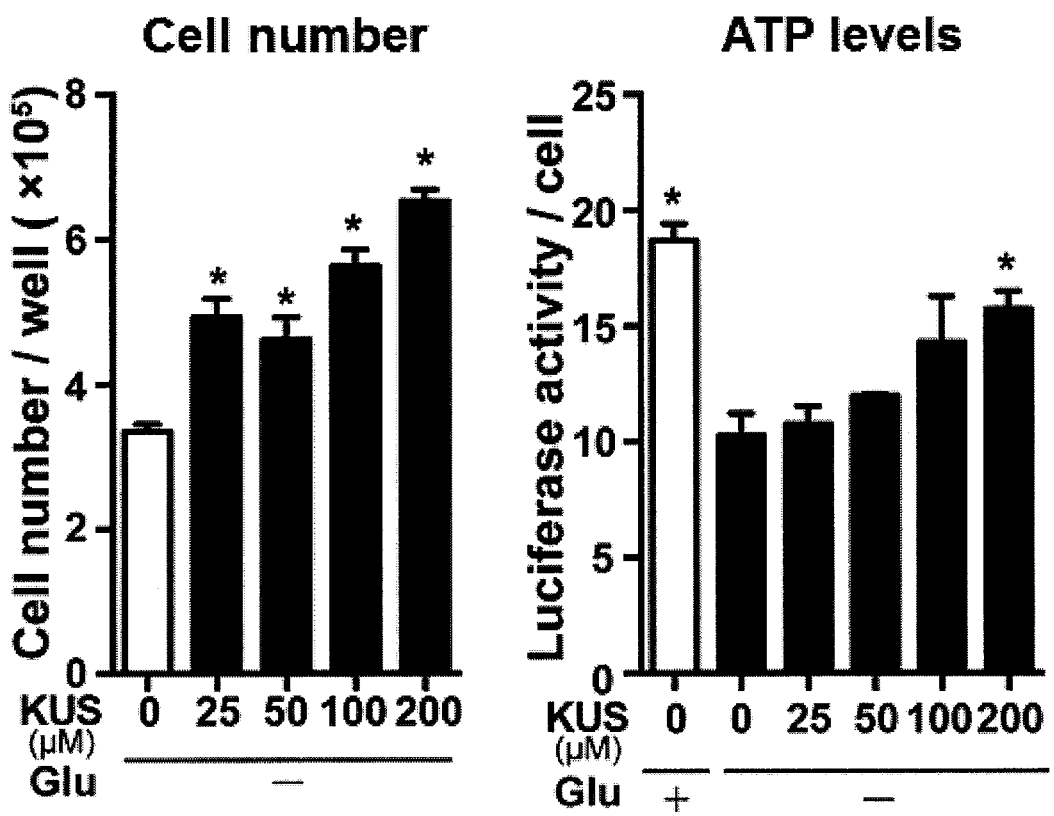
FIG. 6 shows the cell numbers and ATP levels of rat cardiomyoblasts cultured under ER stress by glucose depletion. To KUS121(+) groups 25, 50, 100, or 200 μM KUS121 was added. *: P<0.05 vs. glucose(−) KUS(−)
Figure 7:
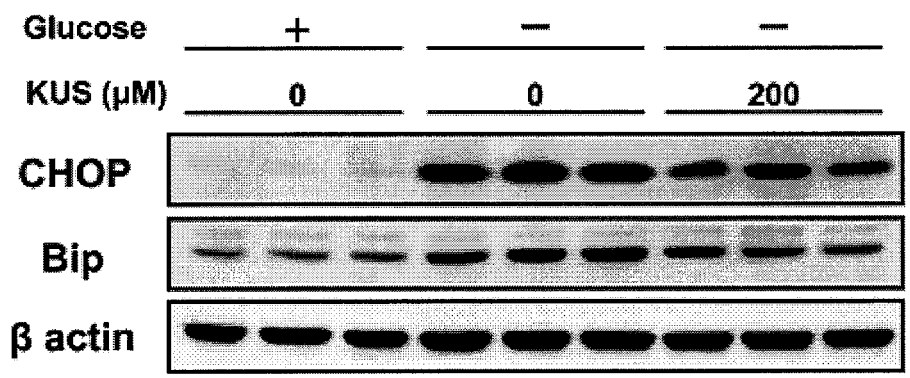
FIG. 7 shows the results of Western blotting of CHOP and Bip in rat cardiomyoblasts cultured under ER stress by glucose depletion. To KUS121(+) group 200 μM KUS121 was added.

Similar experiments were performed using the cells cultured in a glucose-free medium. The results are shown in FIGS. 6 and 7. The cell number was increased depending on the dose of KUS121. The ATP level was decreased in the absence of glucose, but increased depending on the dose of KUS121. The expressions of CHOP and Bip, ER stress markers, were suppressed in the presence of KUS121.

The results suggest that KUS121 suppresses ATP consumption in cardiomyocytes and cardiomyoblasts under ER stress and inhibits cell death by suppressing ER stress.

Test 5: Mouse Cardiac Ischemia and Reperfusion Injury Model (KUS Administration Prior to Ischemia)

Eight-week-old C57BL/6J mice were used. Each mouse was anesthetized with intraperitoneally administered pentobarbital (64.8 mg/kg). An endotracheal tube was introduced after the anesthetic induction and positive pressure ventilation was provided.

Each mouse was fixed in a right lateral position, the thoracic cavity was opened through left thoracotomy in the third intercostal space to expose the heart. The pericardium was slightly detached and the left anterior descending coronary artery was ligated with a 7-0 prolene suture and a PE10 tube at a site 1 or 2 mm closer to the apex of the heart from the left atrial inferior margin. The blockage of the coronary blood flow was confirmed by observing a change in the color of the myocardium. The ischemia was continued for 45 minutes and then reperfusion was induced by removing the PE10 tube. The reperfusion was confirmed by checking restoration of the color of the myocardium. The thoracic cavity was closed with 7-0 prolene sutures and the skin was closed with 4-0 silk sutures. After observing awakening from the anesthesia, the endotracheal tube was removed.

KUS Administration Prior to Ischemia

Figure 8:
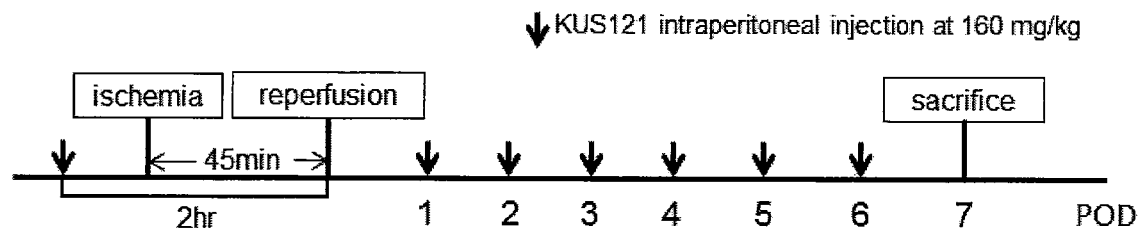
FIG. 8 shows the schematic drawing of the schedule for intraperitoneally administering KUS121 to cardiac ischemia and reperfusion injury model mice prior to ischemia and after reperfusion. KUS121 was intraperitoneally administered at the dose of 160 mg/kg prior to ischemia and every 24 hours after reperfusion.

KUS121 dissolved in a physiological saline was injected prior to the ischemia induction. FIG. 8 shows the schematic drawing of the administration schedule. First, 2 hours before the reperfusion, i.e., about 1 hour before the start of the ischemia, KUS121 was intraperitoneally administered at the dose of 160 mg/kg. Subsequently, KUS121 was intraperitoneally administered at the dose of 160 mg/kg every 24 hours for 6 days.

Histological Analysis

Figure 9:
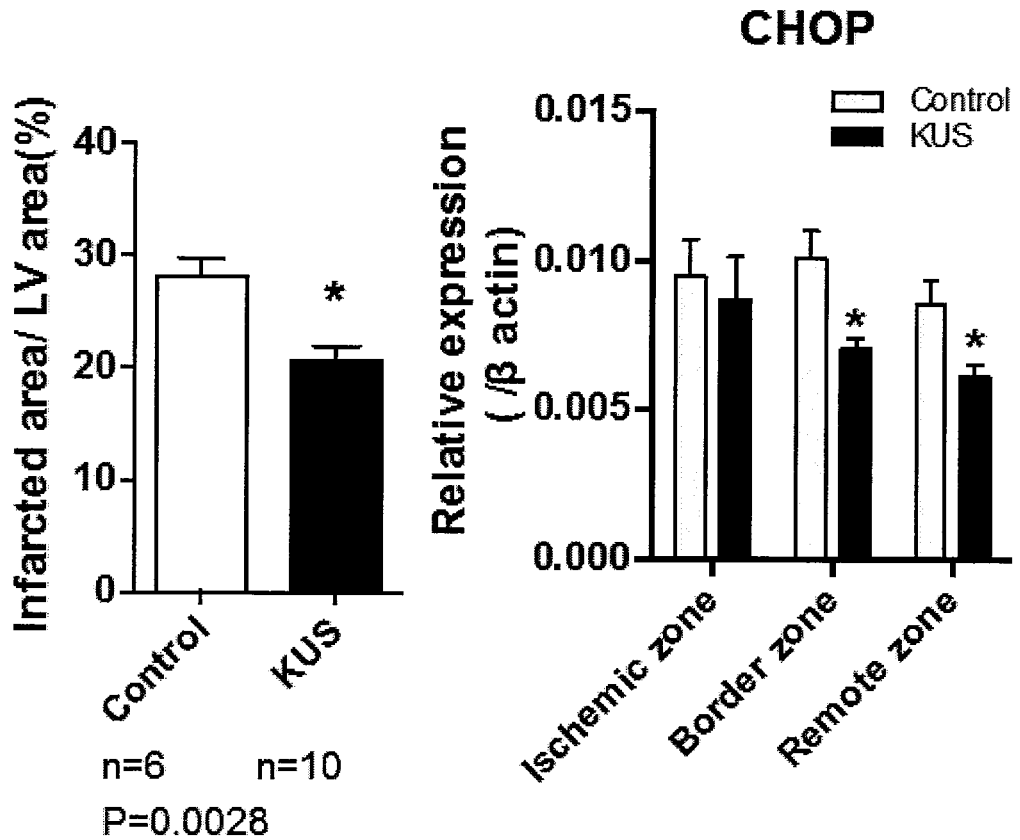
FIG. 9 shows the ratios of infarcted area to left ventricle area and the expression levels of CHOP in cardiac ischemia and reperfusion injury model mice to which KUS121 was intraperitoneally administered prior to ischemia and after reperfusion.

Seven days after the surgery, the mice were anesthetized with pentobarbital, perfused with 4% paraformaldehyde (PFA) for fixation, and the hearts were isolated. The isolated hearts were further fixed in 4% PFA overnight. The hearts were embedded in paraffin and sections were prepared. The infarcted regions were evaluated with Masson's trichrome staining. The images were acquired using a microscope (BZ-9000, Keyence) and the infarcted areas were measured using Image J (NIH). The results are shown in FIG. 9. The infarcted area was smaller in the KUS121 group than in the control group. Western blotting revealed that the expression of CHOP, an ER stress marker, was suppressed in the border zone and non-ischemic zone in the KUS121 group.

Echocardiography

Figure 10:
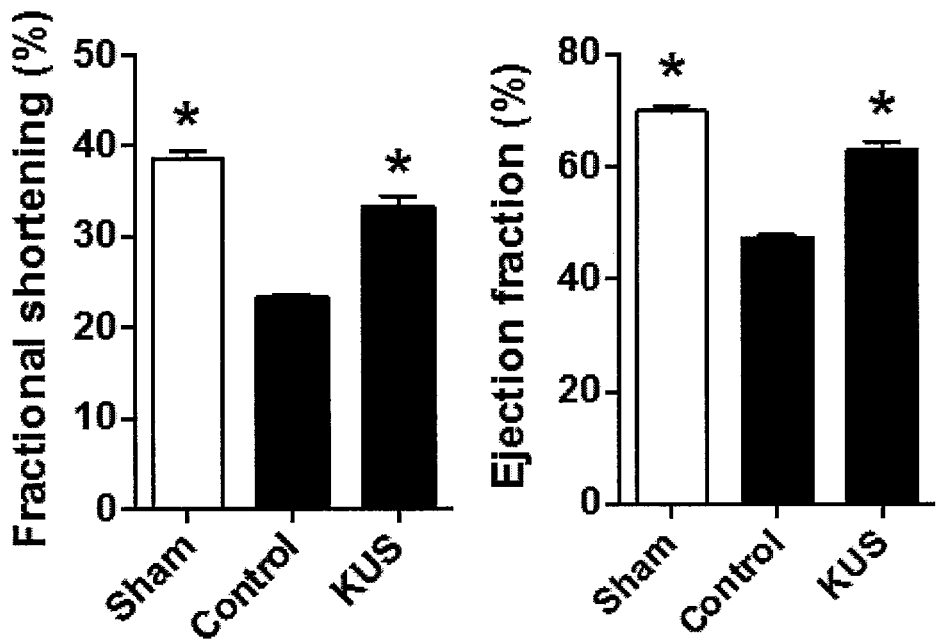
FIG. 10 shows the cardiac functions evaluated in cardiac ischemia and reperfusion injury model mice to which KUS121 was intraperitoneally administered prior to ischemia and after reperfusion. Left panel: left ventricular fractional shortening, Right panel: left ventricular ejection fraction.

To evaluate the cardiac function, echocardiography (Vevo$^{registered\ trademark}$ 2100, VISUALSONICS) was performed in the mouse ischemia and reperfusion injury model. The mice were kept under inhalation anesthesia with 2% isoflurane. The left ventricular systolic functions were evaluated by measuring the left ventricular fractional shortening and left ventricular ejection fraction in parasternal short axis views. The results are shown in FIG. 10. The left ventricular systolic function of the KUS121 group was kept well at almost the same level as that in sham-operated group.

Test 6: Mouse Heart Ischemia and Reperfusion Injury Model (ATP Visualization Mouse)

ATP visualization mouse (A team mouse) generated by Dr. Masamichi Yamamoto (Department of Nephrology, Graduate School of Medicine, Kyoto University) was used. In A team mouse fluorescence resonance energy transfer (FRET) from GFP to OFP occurs depending on the intracellular ATP level. The OFP/GFP ratio is proportional to the ATP level.

Figure 11:
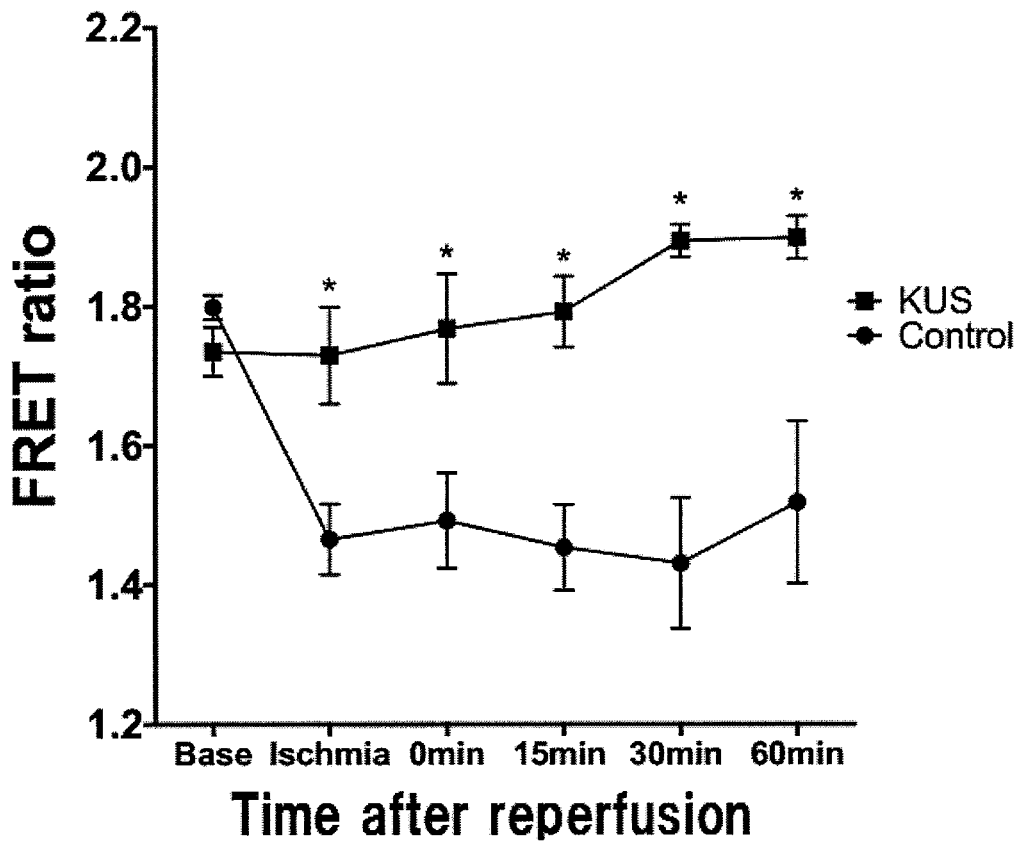
FIG. 11 shows the cardiac ATP levels of cardiac ischemia and reperfusion injury model mice derived from A team mice to which KUS121 was intraperitoneally administered prior to ischemia.

Anesthesia was induced in each A team mouse with 4% isoflurane and maintained with 2% isoflurane during surgery. An endotracheal tube was introduced after the anesthetic induction and positive pressure ventilation was provided. The lateral thoracic regions and subcostal margins were incised bilaterally and the thoracic cavity was opened to expose the heart. The left anterior descending coronary artery was ligated with a 7-0 prolene suture and a PE10 tube at a site 1 or 2 mm closer to the apex of the heart from the left atrial inferior margin. The ischemia was continued for 45 minutes and then reperfusion was induced by removing the PE10 tube. KUS121 was intraperitoneally administered at the dose of 160 mg/kg 2 hours before the reperfusion. For measuring the ATP level, fluorescence was excited at 470/40 and detected at 515/30 for GFP and 575/40 for OFP to acquire images. The OFP/GFP ratios were analyzed using MetaMorph (Molecular Devices). The results are shown in FIG. 11. The ATP level during ischemia was decreased in the control group, but maintained in the KUS121 group.

Test 7: Mouse Cardiac Ischemia and Reperfusion Injury Model (KUS Administration After Reperfusion)

Mouse myocardial infarction model was prepared as in Test 5.

(1) 160 mg/kg

Figure 12:
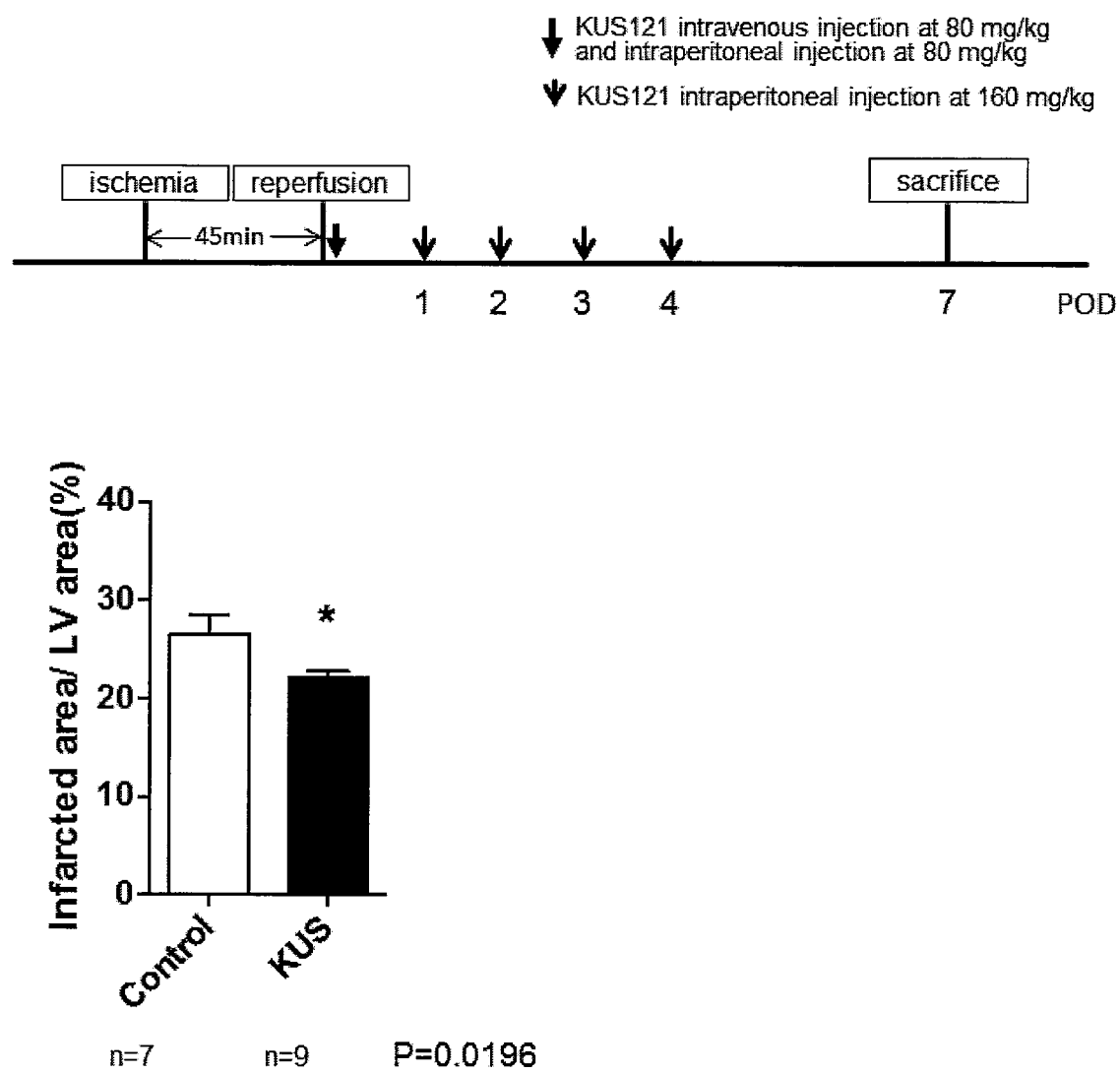
FIG. 12 shows the schedule for administering KUS121 to cardiac ischemia and reperfusion injury model mice after reperfusion and the ratios of infarcted area to left ventricle area determined 7 days after the surgery. KUS121 was administered intravenously at the dose of 80 mg/kg body weight and intraperitoneally at the dose of 80 mg/kg body weight immediately after the reperfusion. Subsequently, KUS121 was intraperitoneally administered at the dose of 160 mg/kg body weight every 24 hours.

First, immediately after the reperfusion KUS121 was administered intravenously at the dose of 80 mg/kg and intraperitoneally at the dose of 80 mg/kg. Subsequently, KUS121 was intraperitoneally administered at the dose of 160 mg/kg every 24 hours for 4 days. Seven days after the surgery, histological analysis was performed as in Test 5 to determine the infarcted area. FIG. 12 shows the schematic drawing of the administration schedule and the results. The infarcted area was smaller in the KUS121 group than in the control group.

(2) 50 mg/kg

Figure 13:
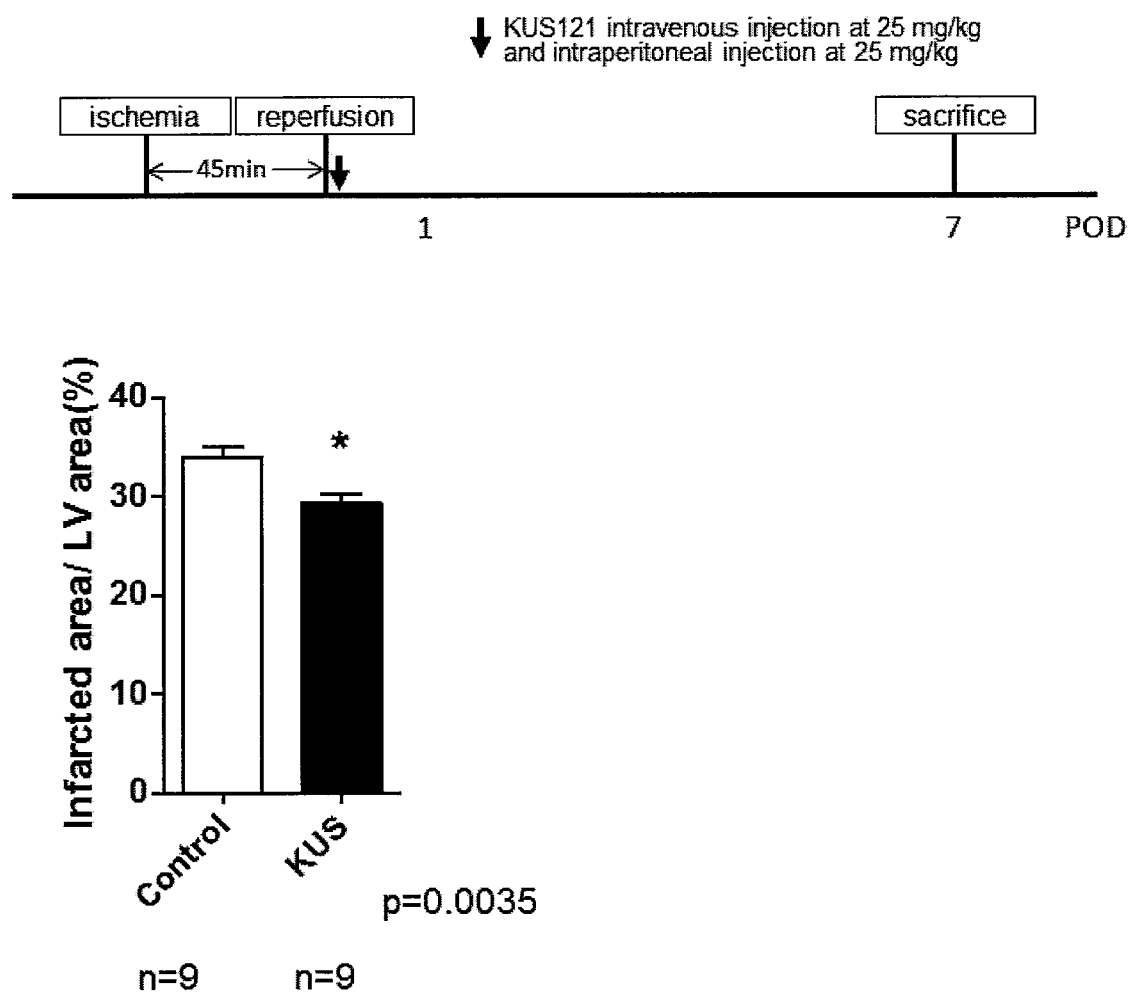
FIG. 13 shows the schedule for administering KUS121 to cardiac ischemia and reperfusion injury model mice after reperfusion and the ratios of infarcted area to left ventricle area determined 7 days after the surgery. KUS121 was administered intravenously at the dose of 25 mg/kg body weight and intraperitoneally at the dose of 25 mg/kg body weight immediately after the reperfusion.

Immediately after the reperfusion KUS121 was administered intravenously at the dose of 25 mg/kg and intraperitoneally at the dose of 25 mg/kg. Subsequently, KUS121 was not administered. Seven days after the surgery, histological analysis was performed as in Test 5 to determine the infarcted area. FIG. 13 shows the schematic drawing of the administration schedule and the results. The infarcted area was smaller in the KUS121 group than in the control group.

(3) 16 mg/kg

Figure 14:
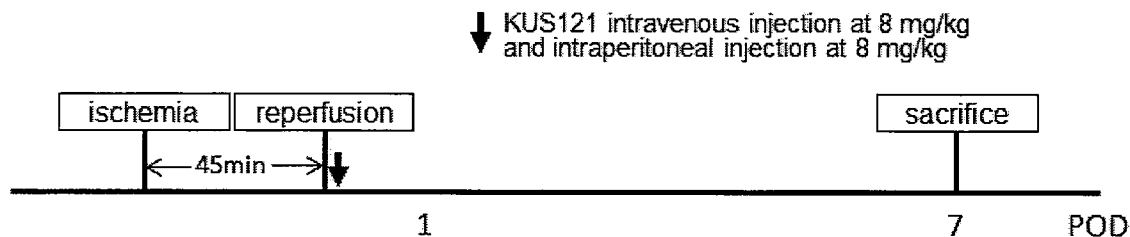
FIG. 14 shows the schedule for administering KUS121 to cardiac ischemia and reperfusion injury model mice after reperfusion and the ratios of infarcted area to left ventricle area determined 7 days after the surgery. KUS121 was administered intravenously at the dose of 8 mg/kg body weight and intraperitoneally at the dose of 8 mg/kg body weight immediately after the reperfusion.
Figure 14:
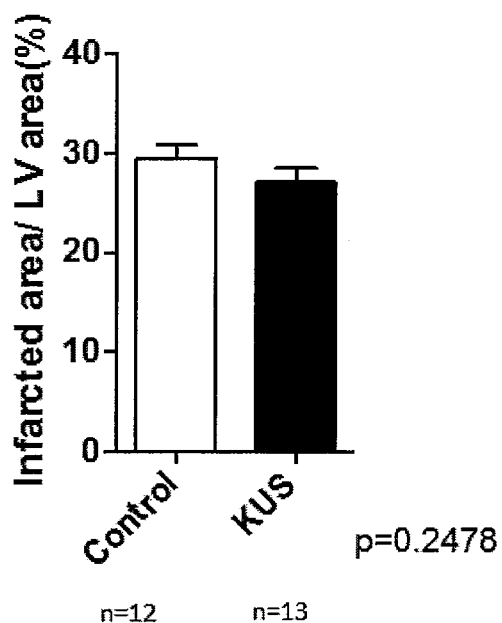

Immediately after the reperfusion KUS121 was administered intravenously at the dose of 8 mg/kg and intraperitoneally at the dose of 8 mg/kg. Subsequently, KUS121 was not administered. Seven days after the surgery, histological analysis was performed as in Test 5 to determine the infarcted area. FIG. 14 shows the schematic drawing of the administration schedule and the results. No significant difference in the infarcted area was observed between the KUS121 group and the control group.

Test 8: Porcine Cardiac Ischemia and Reperfusion Injury Model (Intravenous and Intracoronary Administration of KUS)

Figure 15:
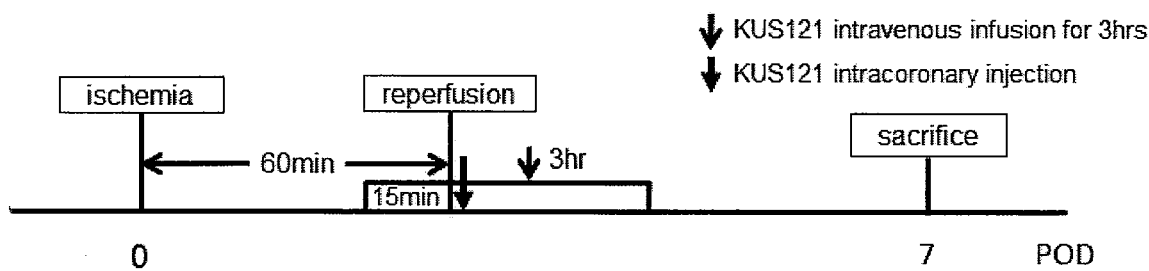
FIG. 15 shows the schematic drawing of the schedule for administering KUS121 to cardiac ischemia and reperfusion injury model pigs. Intravenous infusion of KUS121 at the dose of 4 mg/kg body weight was started 45 minutes after the ischemia and continued for 3 hours. Additionally KUS121 was intracoronarily administered at the dose of 0.16 mg/kg body weight immediately after the reperfusion.

Porcine myocardial infarction model was prepared by inserting a catheter into a Yorkshire pig under general anesthesia and occluding the left coronary artery with a balloon. An infusion solution was prepared by dissolving KUS121 (4 mg/kg) in 250 mL of glucose solution and administered by intravenous infusion that started 45 minutes after the occlusion of the coronary artery and continued for 3 hours. The balloon was released 60 minutes after the occlusion, and 10 mL of the infusion solution was infused intracoronarily. FIG. 15 shows the schematic drawing of the administration schedule.

(1) Infarct Size and Cardiac Function Evaluated by MRI

Figure 16:
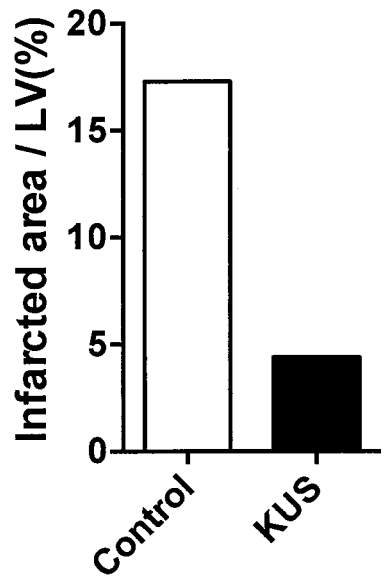
FIG. 16 shows the ratios of infarcted area to left ventricle area in cardiac ischemia and reperfusion injury model pigs.
Figure 17:
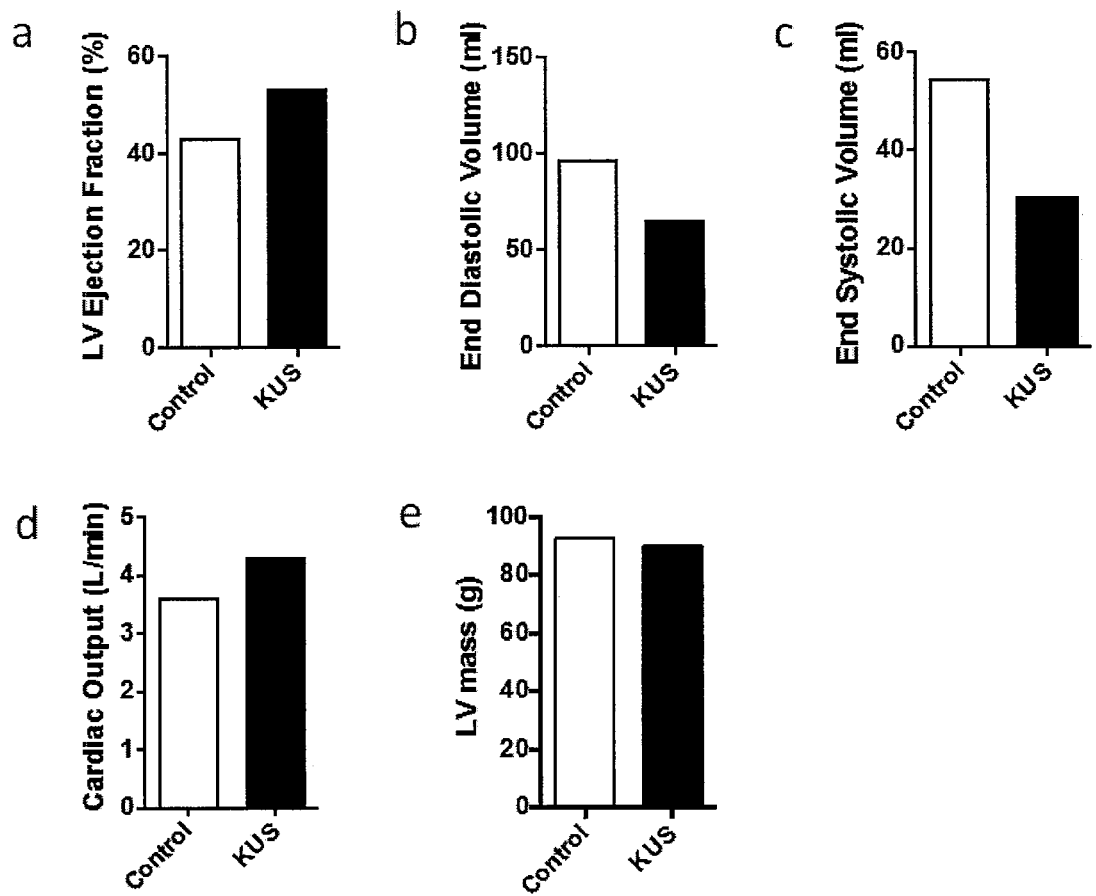
FIG. 17 shows the cardiac functions evaluated in cardiac ischemia and reperfusion injury model pigs. Panel a: left ventricular ejection fraction, Panel b: end diastolic volume, Panel c: end systolic volume, Panel d: cardiac output, Panel e: left ventricular mass.

One week after the occlusion, the infarct size was evaluated by late gadolinium enhanced MRI. FIG. 16 shows the infarcted area per left ventricle. The cardiac function was evaluated by determining left ventricular ejection fraction, end diastolic volume, end systolic volume, cardiac output, and left ventricular mass by MRI. The results are shown in FIG. 17. The left ventricular systolic function was improved by KUS121 administration.

(2) Histological Analysis

Figure 18:
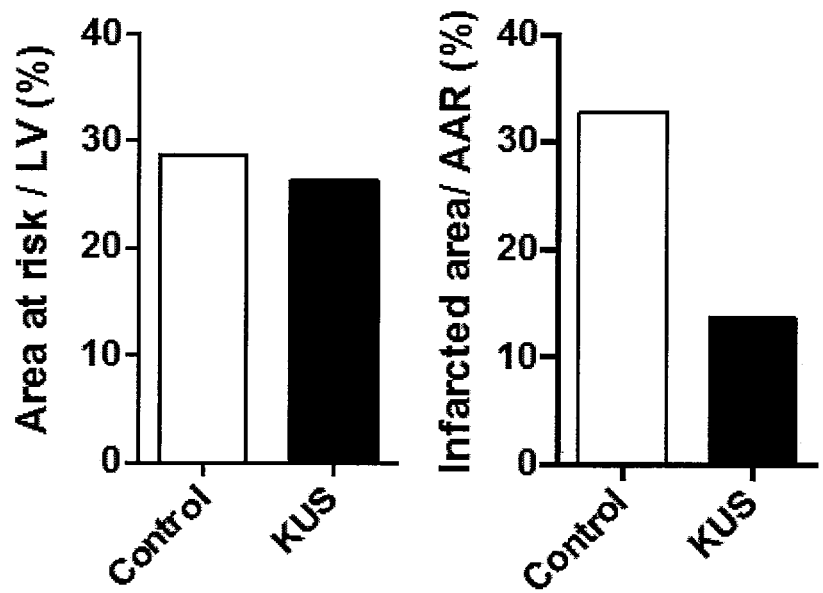
FIG. 18 shows the results of histological analysis in cardiac ischemia and reperfusion injury model pigs. Left panel: area at risk relative to left ventricle, Right panel: infarcted area relative to area at risk.

After the MRI, the occluded part of the left coronary artery was occluded again with the balloon catheter and 1% Evans blue was injected to the left and right coronary arteries (60 mL for the left coronary artery and 30 mL for the right coronary artery; non-infarct regions were stained blue). Additionally, 30 mL of 1% TTC solution was injected through the guidewire lumen of the occlusion balloon. Euthanasia was then performed by an intravenous injection of potassium chloride. The heart was isolated and 10-mm thick sections were prepared parallel to the atrioventricular groove. The sections were further immersed in 1% TTC solution for 10 minutes at 37° C. (regions not damaged by myocardial infarction were stained red). All sections were weighed and photographed. They were fixed in 10% formaldehyde and used for subsequent histological analysis. The results are shown in FIG. 18. The left graph shows the area at risk relative to the left ventricle and the right graph shows the infarcted area relative to the area at risk. No difference was found in the area at risk between the sham-operated group and the KUS group, but administration of KUS decreased the infarcted area per area at risk.

Test 9: Porcine Cardiac Ischemia and Reperfusion Injury Model (KUS Administration After Reperfusion)

Figure 19:
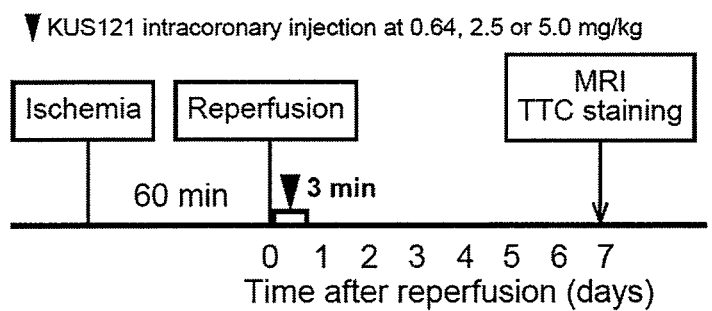
FIG. 19 shows the schedule of intracoronary administration of KUS121 in cardiac ischemia and reperfusion injury model pigs after reperfusion, the ratios of infarcted area to left ventricle (left), the ratios of area at risk to left ventricle (middle), and the ratios of infarcted area to area at risk (right). KUS121 was intracoronarily administered at the dose of 0.64, 2.5, or 5.0 mg/kg body weight after the reperfusion.
Figure 19:
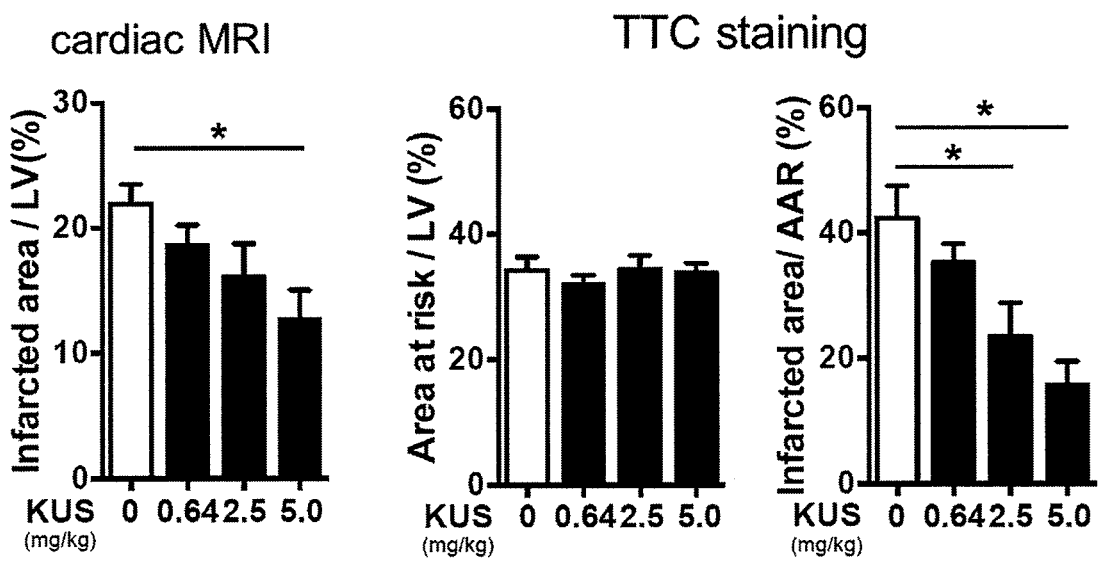

Porcine myocardial infarction model was prepared as in Test 8. The balloon was released 60 minutes after the occlusion, and immediately KUS121 was administered by intracoronary injection at a dose of 0.64, 2.5, or 5.0 mg/kg for 3 minutes. Seven days after the surgery, the infarct size was evaluated by MRI and the infarcted area was determined by histological analysis as in Test 8. FIG. 19 shows the schematic drawing of the administration schedule and the results. The ratio of infarcted area/left ventricle (LV) area evaluated by MRI was decreased in the KUS121 group in a dose-dependent manner. The ratio of infarcted area/area at risk (AAR) of the KUS121 group was comparable with that of the control group. The ratio of infarcted area/AAR was decreased in the KUS121 group in a dose-dependent manner. The appearance of the infarcted regions visualized by Masson's trichrome staining was comparable to that visualized by TTC staining. The data indicate that intracoronary administration of KUS121 after a cardiac damage provides a significant benefit in the porcine myocardial infarction model.

The results of Tests 1 to 9 suggest that the compounds of formula (I) protect cardiomyocytes and suppress cell death during ischemia-reperfusion and thus are effective for treating myocardial infarction.

INDUSTRIAL APPLICABILITY

The disclosure provides a method for protecting cardiomyocytes and may be used in the field of medicine. For example, the method may be used for treating and preventing diseases associated with cardiomyocyte death, especially for treating myocardial infarction.

What is claimed is:

1. A method of protecting a cardiomyocyte in a subject in need thereof, the method comprising administering a therapeutically effective amount of a compound of formula (I):

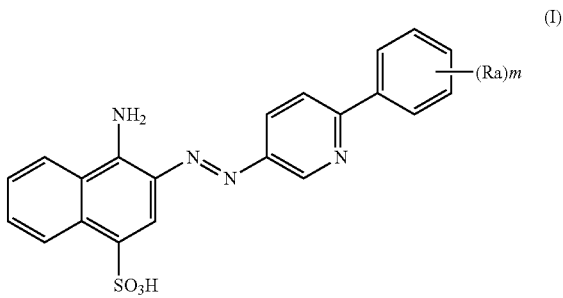

wherein

Ra is selected from the group consisting of halo, hydroxy, alkyl, halo-substituted alkyl, aryl, halo- or alkyl-substituted aryl, alkoxy, hydroxy- or carboxy-substituted alkoxy, aryloxy, halo- or alkyl-substituted aryloxy, CHO, C(O)-alkyl, C(O)-aryl, C(O)-alkyl-carboxyl, C(O)-alkylene-carboxy ester, and cyano, and m is an integer selected from 0 to 4, or an ester, oxide, pharmaceutically acceptable salt or solvate thereof to the subject.

2. The method according to claim 1, wherein the protecting a cardiomyocyte comprises suppressing death of the cardiomyocyte.

3. The method according to claim 1, wherein each Ra radical is independently selected from the group consisting of halo, hydroxy, alkyl, halo-substituted alkyl, and alkoxy.

4. The method according to claim 1, wherein the compound of formula (I) is selected from the group consisting of
4-amino-3-(6-phenylpyridine-3-ylazo)naphthalene-1-sulfonic acid;
4-amino-3-(6-p-tolylpyridine-3-ylazo)naphthalene-1-sulfonic acid;
4-amino-3-(6-m-tolylpyridine-3-ylazo)naphthalene-1-sulfonic acid;
4-amino-3-(6-o-tolylpyridine-3-ylazo)naphthalene-1-sulfonic acid;
4-amino-3-(6-biphenyl-2-ylpyridine-3-ylazo)naphthalene-1-sulfonic acid;
3-[6-(2-acetylphenyl)pyridine-3-ylazo]-4-aminonaphthalene-1-sulfonic acid;
3-[6-(3-acetylphenyl)pyridine-3-ylazo]-4-aminonaphthalene-1-sulfonic acid;
3-[6-(4-acetylphenyl)pyridine-3-ylazo]-4-aminonaphthalenesulfonic acid;
4-amino-3-[6-(2,4-dichlorophenyl)pyridine-3-ylazo]naphthalene-1-sulfonic acid;
4-amino-3-[6-(2-trifluoromethylphenyl)pyridine-3-ylazo]naphthalene-1-sulfonic acid;
4-amino-3-[6-(4-trifluoromethylphenyl)pyridine-3-ylazo]naphthalene-1-sulfonic acid;
4-amino-3-[6-(2-chlorophenyl)pyridine-3-ylazo]naphthalene-1-sulfonic acid;
4-amino-3-[6-(3-chlorophenyl)pyridine-3-ylazo]naphthalene-1-sulfonic acid;
4-amino-3-[6-(4-chlorophenyl)pyridine-3-ylazo]naphthalene-1-sulfonic acid;
4-amino-3-[6-(2-methoxyphenyl)pyridine-3-ylazo]naphthalene-1-sulfonic acid;
4-amino-3-[6-(4-methoxyphenyl)pyridine-3-ylazo]naphthalene-1-sulfonic acid;
4-amino-3-[6-(2-isopropoxyphenyl)pyridine-3-ylazo]naphthalene-1-sulfonic acid;
4-amino-3-[6-(4-isopropoxyphenyl)pyridine-3-ylazo]naphthalene-1-sulfonic acid;
4-amino-3-[6-(2-phenoxyphenyl)pyridine-3-ylazo]naphthalene-1-sulfonic acid;
4-amino-3-[6-(3-methoxyphenyl)pyridine-3-ylazo]naphthalene-1-sulfonic acid;
4-amino-3-[6-(2,3-dimethylphenyl)pyridine-3-ylazo]naphthalene-1-sulfonic acid;
4-amino-3-[6-(2,5-dimethylphenyl)pyridine-3-ylazo]naphthalene-1-sulfonic acid;
4-amino-3-[6-(3,5-dimethylphenyl)pyridine-3-ylazo]naphthalene-1-sulfonic acid;
4-amino-3-[6-(3-trifluoromethylphenyl)pyridine-3-ylazo]naphthalene-1-sulfonic acid;
4-{4-[5-(1-amino-4-sulfonaphthalene-2-ylazo)pyridine-2-yl]phenyl}-4-oxobutyric acid;
4-amino-3-(6-biphenyl-3-ylpyridine-3-ylazo)naphthalene-1-sulfonic acid;
4-amino-3-[6-(3-cyanophenyl)pyridine-3-ylazo]naphthalene-1-sulfonic acid;
4-amino-3-[6-(4-cyanophenyl)pyridine-3-ylazo]naphthalene-1-sulfonic acid;
4-amino-3-[6-(3,5-bistrifluoromethylphenyl)pyridine-3-ylazo]naphthalenesulfonic acid;
4-amino-3-[6-(4-benzoylphenyl)pyridine-3-ylazo]naphthalene-1-sulfonic acid;
4-amino-3-[6-(2-propoxyphenyl)pyridine-3-ylazo]naphthalene-1-sulfonic acid;
4-amino-3-[6-(4-fluoro-2-methylphenyl)pyridine-3-ylazo]naphthalene-1-sulfonic acid;
4-amino-3-[6-(5-fluoro-2-propoxyphenyl)pyridine-3-ylazo]naphthalene-1-sulfonic acid;
4-amino-3-[6-(2-fluoro-6-propoxyphenyl)pyridine-3-ylazo]naphthalene-1-sulfonic acid;
4-amino-3-[6-(4-fluoro-2-propoxyphenyl)pyridine-3-ylazo]naphthalene-1-sulfonic acid;
4-amino-3-[6-(5-fluoro-2-methylphenyl)pyridine-3-ylazo]naphthalene-1-sulfonic acid;
4-amino-3-[6-(2-fluoro-5-methylphenyl)pyridine-3-ylazo]naphthalene-1-sulfonic acid;
4-amino-3-[6-(2-butoxyphenyl)pyridine-3-ylazo]naphthalene-1-sulfonic acid;
4-amino-3-[6-(2-hexyloxyphenyl)pyridine-3-ylazo]naphthalene-1-sulfonic acid;
4-amino-3-[6-(4-butylphenyl)pyridine-3-ylazo]naphthalene-1-sulfonic acid;
4-amino-3-[6-(2-hydroxyphenyl)pyridine-3-ylazo]naphthalene-1-sulfonic acid;
4-amino-3-{6-[2-(6-hydroxyhexyloxy)phenyl]pyridine-3-ylazo}naphthalene-1-sulfonic acid;
4-{2-[5-(1-amino-4-sulfonaphthalene-2-ylazo)pyridine-2-yl]phenoxyl}butyric acid;
4-amino-3-{6-[2-(3-hydroxypropoxy)phenyl]pyridine-3-ylazo}naphthalene-1-sulfonic acid;
4-amino-3-[6-(2-isobutoxyphenyl)pyridine-3-ylazo]naphthalene-1-sulfonic acid;
4-amino-3-[6-(5-chloro-2-hydroxyphenyl)pyridine-3-ylazo]naphthalene-1-sulfonic acid;
4-amino-3-[6-(4-methylbiphenyl-2-yl)pyridine-3-ylazo]naphthalene-1-sulfonic acid;
4-amino-3-[6-(4'-chloro-4-methylbiphenyl-2-yl)pyridine-3-ylazo]naphthalene-1-sulfonic acid;
4-amino-3-[6-(4,3',5'-trimethylbiphenyl-2-yl)pyridine-3-ylazo]naphthalene-1-sulfonic acid;
4-amino-3-[6-(3'-chloro-4-methylbiphenyl-2-yl)pyridine-3-ylazo]naphthalene-1-sulfonic acid;
4-amino-3-[6-(2,6-dimethylphenyl)pyridine-3-ylazo]naphthalene-1-sulfonic acid;
4-amino-3-[6-(3-formyl-2-isopropoxy-5-methylphenyl)pyridine-3-ylazo]naphthalene-1-sulfonic acid; and
4-amino-3-[6-(3-formyl-2-butoxy-5-methylphenyl)pyridine-3-ylazo]naphthalene-1-sulfonic acid.

5. The method according to claim 1, wherein the compound of formula (I) is 4-amino-3-[6-(4-fluoro-2-methylphenyl)pyridine-3-ylazo]naphthalene-1-sulfonic acid.

6. The method according to claim 1, wherein the compound, or the ester, oxide, pharmaceutically acceptable salt or solvate thereof is administered intracoronarily.

7. The method according to claim 1, wherein the compound, or the ester, oxide, pharmaceutically acceptable salt or solvate thereof is administered during reperfusion after myocardial infarction.

8. The method according to claim 1, wherein a cardiac disease associated with cardiomyocyte death is treated.

9. The method according to claim 8, wherein the cardiac disease associated with cardiomyocyte death is myocardial infarction, chronic heart failure, hypertensive heart failure, or dilated cardiomyopathy.

* * * * *